United States Patent

Flanagan

Patent Number: 5,264,587
Date of Patent: Nov. 23, 1993

[54] METHOD OF PREPARING α-OXOPYRROLO[2,3-B]INDOLE ACETIC ACIDS AND DERIVATIVES

[75] Inventor: Denise M. Flanagan, Bridgewater, N.J.

[73] Assignee: Hoechst-Roussel Pharmaceuticals Incorporated, Somerville, N.J.

[21] Appl. No.: 927,042

[22] Filed: Aug. 10, 1992

Related U.S. Application Data

[60] Division of Ser. No. 765,795, Sep. 26, 1991, Pat. No. 5,173,497, which is a continuation-in-part of Ser. No. 524,627, May 17, 1990, abandoned.

[51] Int. Cl.⁵ .................................. C07D 487/04
[52] U.S. Cl. ............................................. 548/429
[58] Field of Search ...................... 548/429; 514/411

[56] References Cited

PUBLICATIONS

Seebach et al., *Synthesis* Feb. 1982, pp. 138–141.

*Primary Examiner*—Mary C. Lee
*Assistant Examiner*—Mary Susan H. Gabilan
*Attorney, Agent, or Firm*—Elliott Korsen

[57] ABSTRACT

This invention relates to compounds of the formula

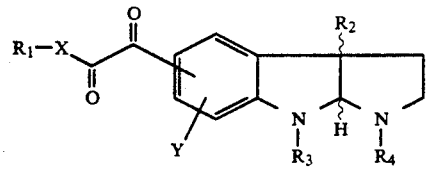

where X is —NH, oxygen, N-loweralkyl, or N-arylloweralkyl; $R_1$ is hydrogen, loweralkyl, cycloalkyl, aryl, arylloweralkyl, loweralkylene, haloloweralkyl, heteroaryl selected from the group consisting of thienyl, furanyl, pyrrolyl and pyridinyl; heteroarylloweralkyl, heterocyclic selected from piperidinyl, piperazinyl, pyrrolidinyl; or heterocyclicloweralkyl; $R_2$ is hydrogen or loweralkyl; $R_3$ is loweralkyl or arylloweralkyl; $R_4$ is hydrogen, loweralkyl, loweralkenyl, loweralkynyl, arylloweralkyl, formyl, loweralkylcarbonyl, arylloweralkylcarbonyl or loweralkoxycarbonyl; Y is hydrogen, loweralkyl or loweralkoxy, and the pharmaceutically acceptable acid addition salts thereof, and where applicable, the geometric and optical isomers and racemic mixtures thereof. The compounds of this invention are useful in the treatment of memory impairment characterized by a cholinergic deficit such as that associated with electroshock-induced amnesia and Alzheimer's disease and other senile dementia.

5 Claims, No Drawings

METHOD OF PREPARING α-OXOPYRROLO[2,3-B]INDOLE ACETIC ACIDS AND DERIVATIVES

This is a division, of application Ser. No. 765,795 filed Sep. 26, 1991, now U.S. Pat. No. 5,173,497, which is a continuation-in-part application of U.S. Ser. No. 524,627, filed May 17, 1990, now abandoned.

This invention relates to compounds of the formula

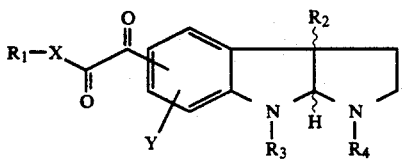

where X is —NH, oxygen, N-loweralkyl, or N-arylloweralkyl; $R_1$ is hydrogen, loweralkyl, cycloalkyl, aryl, arylloweralkyl, loweralkylene, haloloweralkyl, heteroaryl selected from the group consisting of thienyl, furanyl, pyrrolyl and pyridinyl; heteroarylloweralkyl, heterocyclic selected from piperidinyl, piperazinyl, pyrrolidinyl; or heterocycliclohweralkyl; $R_2$ is hydrogen or loweralkyl; $R_3$ is loweralkyl or arylloweralkyl; $R_4$ is hydrogen, loweralkyl, loweralkenyl, loweralkynyl, arylloweralkyl, formyl, loweralkylcarbonyl, arylloweralkylcarbonyl or loweralkoxycarbonyl; Y is hydrogen, loweralkyl or loweralkoxy, and the pharmaceutically acceptable acid addition salts thereof, and where applicable, the geometric and optical isomers and racemic mixtures thereof. The compounds of this invention are useful in the treatment of memory impairment characterized by a cholinergic deficit such as that associated with electroshock-induced amnesia and Alzheimer's disease and other senile dementia.

Subgeneric to the compounds of formula I above are compounds of formula II

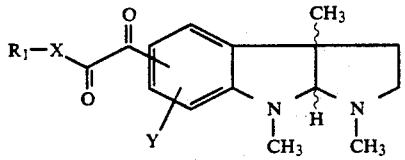

where $R_1$, X and Y are as previously defined.

Throughout the specification and appended claims, a given chemical formula or name shall encompass all geometric and optical isomers and racemic mixtures where such isomers and mixtures exist, as well as pharmaceutically acceptable acid addition salts thereof and solvates thereof such as for instance hydrates.

In the above definition, the term "lower" means the group it is describing contains from 1 to 6 carbon atoms. The term "alkyl" refers to a straight or branched chain hydrocarbon of 1 to 22 carbon atoms, containing no unsaturation, e.g., methyl, ethyl, propyl, iso-propyl, n-butyl, neopentyl, n-hexyl, etc; the term "alkylene" refers to a bivalent radical of the lower branched or unbranched alkyl group it is derived from having valence bonds from two terminal carbons thereof, e.g., methylene (—CH$_2$—), ethylene (—CH$_2$—CH$_2$—), propylene (—CH$_2$CH$_2$CH$_2$—), isopropylene (CH$_3$CHCH$_2$—), etc.; the term "cycloalkyl" refers to a monovalent substituent consisting of a saturated hydrocarbon possessing at least one carbocyclic ring of three to twelve carbon atoms, e.g., cyclopropyl, cyclobutyl, cyclopentyl, cyclohexyl, cycloheptyl, cyclooctyl, etc., having its free valence bond from a carbon of the carbocyclic ring. Said cycloalkyl group may be substituted with 1 or 2 loweralkyl groups, and it may also be substituted at one of the ring carbons so as to form a spiro compound each constituent ring of which being a cycloalkyl of 3 to 8 carbon atoms; the term "arylloweralkyl" refers to a monovalent substituent which consists of an "aryl" group, e.g., phenyl, o-tolyl, m-methoxyphenyl, etc., as defined by the formula

where Z is hydrogen, halogen, loweralkyl, loweralkoxy, trifluoromethyl, nitro, amino and substituted amino, and n is an integer of 1 to 3, linked through a loweralkylene group having its free valence bond from a carbon of the loweralkylene group, and having a formula

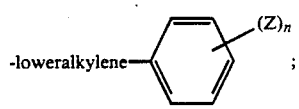

the term "alkenyl" refers to a hydrocarbon group of 1 to 22 carbon atoms having one or more carbon-carbon double bonds, e.g., ethene propene, 1-butene, etc,; the term "alkynyl" refers to a hydrocarbon group of 1 to 22 carbon atoms having one or more carbon-carbon triple bonds, e.g., acetylene, propyne, butyne, pentyne, etc.; the term "heteroaryl" refers to a heterocyclic compound selected from the group consisting of thienyl, furanyl, pyrrolyl and pyridinyl; and the term halogen refers to a member of the halogen family consisting of fluorine, chlorine, bromine and iodine.

In structural formulas depicting compounds involved in this invention, heavy lines ( ◀■ ) coming out of the 3a-carbon and 8a-carbon of the 1,2,3,3a,8,8a-hexahydropyrrolo[2,3-b]indole ring system signify that the two substituents are above the average plane of the three-ring system, whereas dotted lines ( ▬▬▬ ) signify that the two substituents are below the average plane of the three-ring system, and wavy lines ( ∿∿∿ ) signify that the two substituents are both either above or below said average plane. Because of conformational constraints, the two substituents at the 3a- and 8a-positions must be both above said average plane or both below said average plane. Thus, in formulas (I) and (II), the substituents at the 3a- and 8a-carbons are cis inasmuch as they are on the same side of the three ring system. Where said substituents are both above the average plane of the three ring system, the configuration will be referred to as 3aS-cis and where both substituents are below the average plane of the ring, the configuration will be referred to as 3aR-cis.

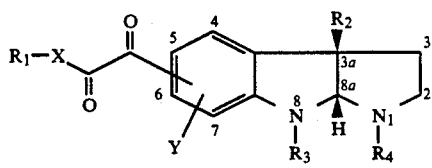

3aS-cis

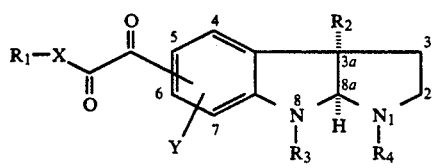

3aR-cis

Throughout the specification and the appended claims, when the inventors intend to designate in a single formula that the compound is 3aS-cis, or 3aR-cis, or a racemic or other mixture of the two, that formula will contain wavy lines as in formula (I).

It is the intent of the present inventors to claim both of said cis isomers, namely, 3aS-cis isomer and 3aR-cis isomer for each compound name or structural formula. It is also the intent of the present inventors to claim all mixtures of the 3aS-cis and 3aR-cis isomers including the racemic mixture (1:1 ratio of 3aS-cis:3aR-cis).

The compounds of this invention are prepared in the following manner. The substituents $R_1$, $R_2$, $R_3$, $R_4$, X and Y are as defined above unless indicated otherwise.

Compound III, the key intermediate, of the formula

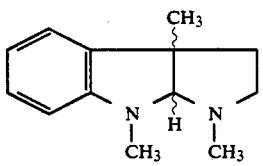

is prepared utilizing generally the synthetic scheme disclosed in Julian et al. J. Chem. Soc., 1935, 563–566 and 755–757, and shown below.

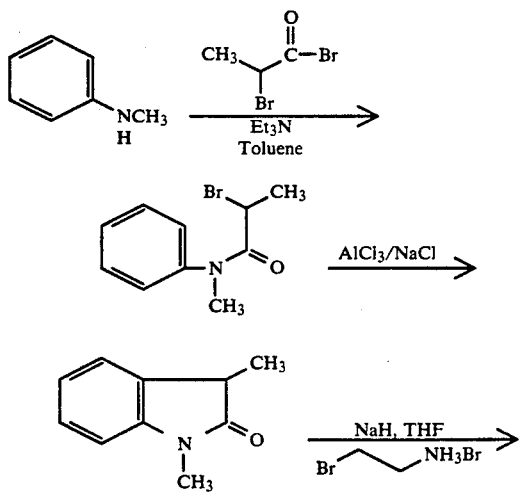

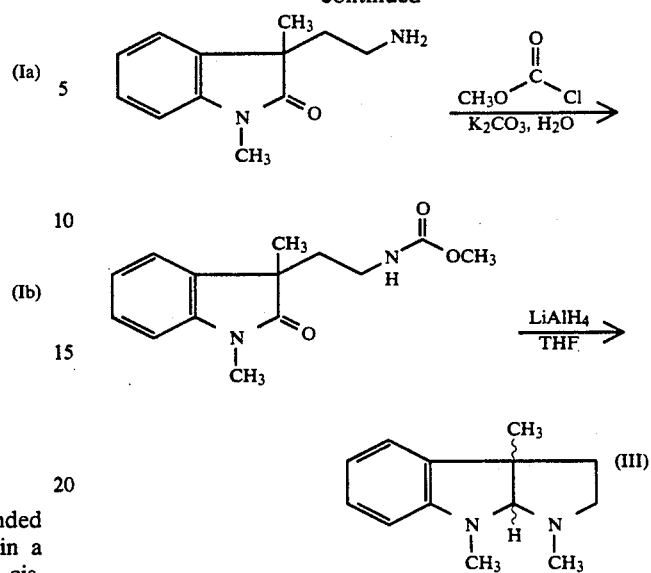

Compound III is allowed to react with pyridinium hydrobromide perbromide of the formula

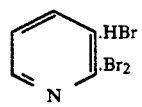

to afford the 5-bromo precursor of the formula

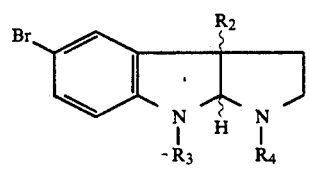

The reaction between Compound III and pyridinium hydrobromide perbromide is typically conducted by preparing a solution of Compound III in a suitable solvent such as methylene chloride, adding a base such as pyridine and subsequently adding the pyridinium hydrobromide perbromide. This reaction typically takes place in an inert atmosphere, i.e., in the presence of nitrogen, at a temperature of −20° to 5° C. for 1 to 5 hours.

To a solution of N,N,N′,N′-tetramethylethylene diamine (TMEDA) of the formula

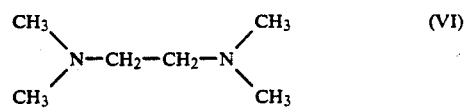

and sec-butyllithium is added Compound IV. This solution is stirred at very low temperature, i.e., −78° to −50° C. for 0.5 to 5 hours. Subsequently this solution is added to a solution of an oxalate bis-ester of the formula

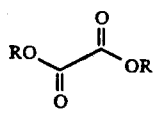

(VII)

where R is alkyl, aryl or aralkyl to afford Compound I of the invention. This reaction typically takes place in the presence of a suitable solvent, such as diethylether.

As an alternative to the above synthesis, titanate-mediated transesterification can be employed for the synthesis of these compounds. This method is described in D. Seebach et al., Synthesis 138 (1982). A compound of the formula

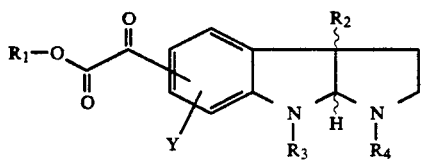

(V)

is reacted with a titanium (IV) alkoxide, i.e. titanium (IV) ethoxide and an alcohol of the formula $R_5$-OH, where $R_5$ is alkyl, aryl, cycloalkyl, arylloweralkyl, loweralkylene, loweralkynyl, heteroaryl selected from the group consisting of thienyl, furanyl, pyrrolyl, pyridinyl or heteroarylloweralkyl. This type of reaction typically takes place at room temperature to just under reflux in an inert atmosphere, i.e., under $N_2$ for 0.5 to 12 hours.

To prepare various amides, compound IV is added to a solution of TMEDA and sec-butyllithium. The solution is stirred at a temperature of $-78°$ C. to $-50°$ C. for 0.5 to 5 hours. Subsequently, this is added to a solution of a mixed oxalate ester amide of the formula

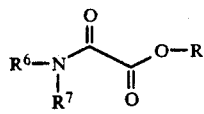

(VIII)

where R, $R^6$ and $R^7$ are alkyl, aryl or aralkyl. This reaction typically takes place in an suitable solvent such as diethylether.

Other well known methods of amide synthesis may be employed.

To prepare the acid analogs of compound I, compound I is treated with an excess of a strong base, e.g., aqueous potassium hydroxide at a temperature of 0° to 5° C. in a lower alkanol solvent such as ethanol, methanol, 1-propanol, etc.. After stirring for 30 minutes the mixture is refluxed for 3 hours. After cooling, the mixture is neutralized with 1N HCl solution.

The compounds of this invention are useful in the treatment of memory impairment characterized by a cholinergic deficit such as that associated with electroshock-induced amnesia and Alzheimer's disease and other senile dementia.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. We have determined in vitro inhibition of acetylcholinesterase activity in rat striatum according to the method described below.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in the brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anticholinesterase activity. This is a modification of the method of Ellman et al., Biochem. Pharmacol. 7, 88 (1961).

PROCEDURE

A. Reagents 1. 0.05M Phosphate buffer, pH 7.2
  (a) 6.85 g $NaH_2PO_4 \cdot H_2O$/100 ml distilled $H_2O$
  (b) 13.40 g $Na_2HPO_4 \cdot 7H_2O$/100 ml distilled $H_2O$
  (c) add (a) to (b) until pH reaches 7.2
  (d) Dilute 1:10
2. Substrate in buffer
  (a) 198 mg acetylthiocholine chloride (10 mM)
  (b) q.s. to 100 ml with 0.05M $NaPO_4$, pH 7.2 (reagent 1)
3. DTNB in buffer
  (a) 19.8 mg 5,5-dithiobisnitrobenzoic acid (DTNB) (0.5 mM)
  (b) q.s. to 100 ml with 0.05M $NaPO_4$, pH 7.2 (reagent 1)
4. A 2 mM stock solution of the test drug is made up in a suitable solvent and q.s. to volume with 0.5 mM DTNB (reagent 3). Drugs are serially diluted (1:10) such that the final concentration (in cuvette) is $10^{-4}M$ and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 25 microliter aliquot of the homogenate is added to 1 ml of vehicle or various concentrations of the test drug and preincubated for 10 minutes at 37° C.

C. Assay

Enzyme activity is measured with the Beckman DU-50 spectrophotometer.

This method can be used for $IC_{50}$ determinations and for measuring kinetic constants.

Instrument Settings

Kinetics Soft-Pac Module TM 598273 (10)
Program TM 6 Kindata:
Source-Vis
Wavelength-412 nm
Sipper-none
Cuvettes-2 ml cuvettes using auto 6-sampler
Blank-1 for each substrate concentration
Interval time-15 seconds (15 or 30 seconds for kinetics)
Total time-5 minutes (5 or 10 minutes for kinetics)
Plot-yes
Span-autoscale
Slope-increasing
Results-yes (gives slope)
Factor-1

Reagents are added to the blank and sample cuvettes as follows:
Blank: 0.8 ml Phosphate Buffer/DTNB 0.8 ml Buffer/Substrate
Control: 0.8 ml Phosphate Buffer/DTNB/Enzyme 0.8 ml Phosphate Buffer/Substrate
Drug: 0.8 ml Phosphate Buffer/DTNB/Drug Enzyme 0.8 ml Phosphate Buffer/Substrate Blank values are determined for each run to control non enzymatic hydrolysis of substrate and these values are automatically substracted by the kindata program available on kinetics soft-pac module. This program also calculates the rate of absorbance change for each cuvette.

For IC$_{50}$ Determinations

Substrate concentration is 10 mM diluted 1:2 in assay yielding final concentration of 5 mM. DTNB concentration is 0.5 mM yielding 0.25 mM final concentration $$\% \text{ Inhibition} = \frac{\text{slope control} - \text{slope drug}}{\text{slope control}} \times 100$$

IC$_{50}$ values are calculated from log-probit analysis.
Results of some of the compounds of this invention and physostigmine (reference) are presented in Table 1.

TABLE 1

| Inhibition of Brain Acetylcholinesterase Activity | |
|---|---|
| Compound | Inhibitory Concentration (IC$_{50}$) ($\mu$M) Brain AChE |
| 1,2,3,3a,8,8a-hexahydro-α-oxo-1,3a,8-trimethyl-5-pyrrolo[2,3-b]indole acetic acid, n-butyl ester | 5.7 |
| 1,2,3,3a,8,8a-hexahydro-α-oxo-1,3a,8-trimethyl-5-pyrrolo[2,3-b]indole acetic acid, n-pentyl ester | 8.0 |
| 1,2,3,3a,8,8a-hexahydro-α-oxo-1,3a,8-trimethyl-5-pyrrolo[2,3-b]indole acetic acid, phenylmethyl ester | 4.4 |
| 1,2,3,3a,8,8a-hexahydro-α-oxo-1,3a,8-trimethyl-5-pyrrolo[2,3-b]indole acetime acid, phenylethyl ester | 9.1 |
| Physostigmine (Reference Compound) | 0.006 |

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the present of a group of animals in which the effect of scopolamine is blocked, as manifested by an increased interval between being placed in the test chamber and re-entering the dark compartment.

Results of this assay for some of the compounds of this invention and those for tacrine and pilocarpine (reference compounds) are presented in Table 2.

TABLE 2

| Compound | Dose (mg/kg of body weight, s.c.) | % of Animals with Scopolamine Induced Memory Deficit Reversal |
|---|---|---|
| 1,2,3,3a,8,8a-hexahydro-α-oxo-1,3a,8-trimethyl-5-pyrrolo-[2,3-b]indole acetic acid, phenylethyl ester | 0.1 | 29 |
| | 0.3 | 36 |
| | 1.0 | 20 |
| (Reference Compounds) | | |
| Tacrine | 0.63 | 13 |
| Pilocarpine | 5.0 | 13 |

Effective amounts of the present invention may be administered to a subject by any one of various methods, for example, orally as in capsules or tablets, parentally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as malic, tartaric, citric, acetic, succinic, maleic, fumaric, oxalic, and salicyclic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0-300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ™, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the doseage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of the invention include:

1,2,3,3a,8,8a-hexahydro-α-oxo-1,3a,8-trimethyl-5-pyrrolo[2,3-b]indole acetic acid, ethyl ester;

1,2,3,3a,8,8a-hexahydro-α-oxo-1,3a,8-trimethyl-5-pyrrolo[2,3-b]indole acetic acid, n-butyl ester;

1,2,3,3a,8,8a-hexahydro-α-oxo-1,3a,8-trimethyl-5-pyrrolo[2,3-b]indole acetic acid, phenylmethyl ester;

1,2,3,3a,8,8a-hexahydro-α-oxo-1,3a,8-trimethyl-5-pyrrolo[2,3-b]indole acetic acid, phenylethyl ester;

1,2,3,3a,8,8a-hexahydro-α-oxo-1,3a,8-trimethyl-5-pyrrolo[2,3-b]indole acetic acid, isopropyl ester;

1,2,3,3a,8,8a-hexahydro-α-oxo-1,3a,8-trimethyl-5-pyrrolo[2,3-b]indole acetic acid, 4-methoxyphenylmethyl ester;

1,2,3,3a,8,8a-hexahydro-α-oxo-1,3a,8-trimethyl-5-pyrrolo[2,3-b]indole acetic acid, 4-chlorophenylethyl ester;

1,2,3,3a,8,8a-hexahydro-α-oxo-1,3a,8-trimethyl-5-pyrrolo[2,3-b]indole acetic acid, n-pentyl ester;

1,2,3,3a,8,8a-hexahydro-α-oxo-1,3a,8-trimethyl-5-pyrrolo[2,3-b]indole acetic acid, n-hexyl ester;

1,2,3,3a,8,8a-hexahydro-α-oxo-1,3a,8-trimethyl-5-pyrrolo[2,3-b]indole acetic acid, n-heptyl ester;

1,2,3,3a,8,8a-hexahydro-α-oxo-1,3a,8-trimethyl-5-pyrrolo[2,3-b]indole acetic acid, n-octyl ester;

7-Bromo-1,2,3,3a,8,8a-hexahydro-α-oxo-1,3a,8-trimethyl-5-pyrrolo[2,3-b]indole acetic acid, ethyl ester;

7-Chloro-1,2,3,3a,8,8a-hexahydro-α-oxo-1,3a,8-trimethyl-5-pyrrolo[2,3-b]indole acetic acid, butyl ester;

1-acetyl-3a,8-dimethyl-1,2,3,3a,8,8a-hexahydro-α-oxo-5-pyrrolo[2,3-b]indole acetic acid, ethyl ester;

1,2,3,3a,8,8a-hexahydro-α-oxo-1,3a,8-trimethyl-5-pyrrolo[2,3-b]indole acetic acid;

1,2,3,3a,8,8a-hexahydro-α-oxo-1,3a,8-trimethyl-5-pyrrolo[2,3-b]indole acetic acid, diisopropyl amide;

1,2,3,3a,8,8a-hexahydro-α-oxo-1,3a,8-trimethyl-5-pyrrolo[2,3-b]indole acetic acid, diethyl amide;

1,2,3,3a,8,8a-hexahydro-α-oxo-1,3a,8-trimethyl-5-pyrrolo[2,3-b]indole acetic acid, N-ethyl-N-phenylmethyl amide;

1,2,3,3a,8,8a-hexahydro-α-oxo-1,3a,8-trimethyl-5-pyrrolo[2,3-b]indole acetic acid, 4-chloro-1-butyl ester;

1,2,3,3a,8,8a-hexahydro-α-oxo-1,3a,8-trimethyl-5-pyrrolo[2,3-b]indole acetic acid, phenylethyl amide;

1,2,3,3a,8,8a-hexahydro-α-oxo-1,3a,8-trimethyl-5-pyrrolo[2,3-b]indole acetic acid, n-butyl amide; and 1,2,3,3a,8,8a-hexahydro-α-oxo-1,3a,8-trimethyl-5-pyrrolo[2,3-b]indole acetic acid, 2,2,2-trifluoroethyl ester, The following examples are for illustrative purposes only and are not to be construed as limiting the invention. All temperatures are given in degrees centigrade (°C.) unless otherwise designated.

EXAMPLE 1

5-Bromo-1,2,3,3a,8,8a-hexahydro-1,3a,8-trimethylpyrrolo[2,3-b]indole

To a chilled (0° C.) solution of 1,2,3,3a,8,8-hexahydro-1,3a,8-trimethylpyrrolo[2,3-b]indole (1.41 g) in methylene chloride (20 ml) was added pyridine (1.41 ml) under an atmosphere of $N_2$. Solid pyridinium hydrobromide perbromide (2.23 g) was added with stirring to the mixture and the resulting solution was maintained at 0° C. for 1 hour. The mixture was poured into water (100 ml) and the aqueous and organic phases separated. The organic phase was washed twice with 50 ml portions of brine and 50 ml portions of saturated sodium bicarbonate and then with 50 ml of brine. After drying the organic phase over $Na_2SO_4$ and filtering, the solvent was removed under reduced pressure. The resulting oil was purified using column chromatography on silica gel with 10% methanol in ethyl acetate as eluent. The appropriate fractions were combined, evaporated and repurified using column chromatography on silica gel with 5% methanol in ethyl acetate as eluant to afford 1.5 g of 5-bromo-1,2,3,3a,8,8a-hexahydro-1,3a,8-trimethylpyrrolo[2,3-b]indole, as an oil.

| Analysis: | | | |
|---|---|---|---|
| Calculated for $C_{13}H_{17}BrN_2$: | 55.53% C | 6.09% H | 9.96% N |
| Found: | 55.33% C | 6.21% H | 9.69% N |

EXAMPLE 2

1,2,3,3a,8,8a-Hexahydro-α-oxo-1,3a,8-trimethyl-5-pyrrolo[2,3-b]indole acetic acid, ethyl ester Tetramethylethylenediamine (TMEDA) (2.3 ml) and s-butyllithium (1.3M in cyclohexane, 11.7 ml) were added to anhydrous ether (8.0 ml) at −78° C. under nitrogen. A solution of 5-bromo-1,2,3,3a,8,8a-hexahydro-1,3a,8-trimethylpyrrolo[2,3-b]indole (3.57 g) in anhydrous ether (10 ml) was added to the resulting reaction mixture at −78° C. via canula and stirred at this temperature for 1 hour and at −20° C. for 1 hour. The solution was then added via canula to a −78° C. solution of diethyloxalate (5.2 ml) in anhydrous ether (30 ml) under $N_2$. The resulting mixture was held at −78° C. for 30 min, −20° C. for 2 hours and room temperature for 30 min. Saturated ammonium chloride solution (10 ml) was added and the organic and aqueous phases separated. The organic phase was washed twice with brine, dried ($Na_2SO_4$), filtered and concentrated under vacuum. The crude residue was purified using preparative high performance liquid chromatography (HPLC), (silica gel, sample loaded and eluted with 2% methanol in ethyl acetate). Concentration of the appropriate fractions afforded 1.6 g of 1,2,3,3a,8,8a-hexahydro-α-oxo-1,3a,8-trimethyl-5-pyrrolo[2,3-b]indole acetic acid, ethyl ester, as an oil.

| Analysis: | | | |
|---|---|---|---|
| Calculated for $C_{17}H_{22}N_2O_3$: | 67.53% C | 7.33% H | 9.26% N |
| Found: | 67.21% C | 7.35% H | 9.15% N |

EXAMPLE 3

1,2,3,3a,8,8a-Hexahydro-α-oxo-1,3a,8-trimethyl-5-pyrrolo[2,3-b]indole acetic acid, n-butyl ester To a nitrogen purged 100 ml 3 neck round bottom flask was added anhydrous tetrahydrofuran (THF) (7.0 ml). Sec-butyllithium (1.3M in cyclohexane, 8.9 ml) was then added, the solution cooled to −78° C. and treated with TMEDA (1.6 ml; 11.0 mmol). A solution of 5-bromo-1,2,3,3a,8,8a-hexahydro-1,3a,8-trimethylpyrrolo[2,3-b]indole (2.50 g) in anhydrous THF (6.0 ml) was added via canula and the mixture stirred at −78° C. for 1½ hours and −20° C. for 1 hour. The resulting solution was then added via canula to a solution of freshly distilled dibutyl oxalate (5.5 ml) in THF (9.0 ml) at −78° C. and maintained at this temperature with stirring for 1 hour. After allowing the mixture to slowly come to room temperature, saturated ammonium chloride solution (10 ml) was added and the solvent removed under reduced pressure. The product was purified by preparative HPLC (silica gel, eluted with 10% methanol in ethyl acetate). The appropriate fractions were combined and evaporated to give 0.51 g of an oil, which upon trituration with hexane afforded 1,2,3,3a,8,8a-hexahydro-α-oxo-1,3a,8-trimethyl-5-pyrrolo[2,3]indole acetic acid, n-butyl ester, as a solid, m.p. 56°-61° C.

Analysis:

| Analysis: | | | |
|---|---|---|---|
| Calculated for $C_{19}H_{26}N_2O_3$: | 69.06% C | 7.93% H | 8.48% N |
| Found: | 68.91% C | 8.0% H | 8.10% N |

EXAMPLE 4

1,2,3,3a,8,8a-Hexahydro-α-oxo-1,3a,8-trimethyl-5-pyrrolo[2,3-b]indole acetic acid, phenylmethyl ester To a chilled (0° C.), stirred solution of 1,2,3,3a,8,8a-hexahydro-α-oxo-1,3a,8-trimethyl-5-pyrrolo[2,3-]indole acetic acid, ethyl ester (0.5 g) in anhydrous benzyl alcohol (10 ml) was added, via syringe, titanium (IV) ethoxide (0.15 ml). The solution was warmed to room temperature and then refluxed under $N_2$ for 2½ hours. The reaction appeared complete by thin layer chromatography (TLC hereafter) (silica gel, 10% methanol in ethyl acetate). The benzyl alcohol was removed by distillation under high vacuum. The residue was dissolved in ethyl acetate (80 ml) and washed successively with two 50 ml portions of saturated aqueous $NH_4Cl$, two 50 ml portions of saturated aqueous $NaHCO_3$ and two 50 ml portions of brine. The organic phase was dried ($Na_2SO_4$), filtered, and the solvent removed under vacuum on a rotary evaporator. The residue, an oil, was purified using preparative HPLC (silica gel, 5% methanol in ethyl acetate as the loading solvent and eluent). The appropriate fractions were combined and the solvents removed under reduced pressure yielding 0.52 g of an oil, which solidified upon standing to give 1,2,3,3a,8,8a-hexahydro-α-oxo-1,3a,8-trimethyl-5-pyrrolo[2,3-b]indole acetic acid phenylmethyl ester, m.p. 53°-57° C.

| Analysis: | | | |
|---|---|---|---|
| Calculated for $C_{22}H_{24}N_2O_3$: | 72.51% C | 6.64% H | 7.69% N |
| Found: | 72.18% C | 6.59% H | 7.52% N |

EXAMPLE 5

1,2,3,3a,8,8a-Hexahydro-α-oxo-1,3a,8-trimethyl-5-pyrrolo[2,3-b]indole acetic acid, phenylethyl ester To a chilled (0° C.) solution of 1,2,3,3a,8,8a-hexahydro-α-oxo-1,3a,8-trimethyl-5-pyrrolo[2,3-b]indole acetic acid, ethyl ester (0.76 g) in anhydrous phenylethyl alcohol (18.1 ml) was added titanium (IV) ethoxide (0.22 ml) via syringe under a nitrogen atmosphere. The solution was warmed to room temperature and heated to just under reflux for 3 hours. The solution was then cooled to 0° C. and saturated $NH_4Cl$ solution was added slowly until a precipitate formed. Methylene chloride (200 ml) was then added and the mixture extracted twice with 100 ml portions of saturated aqueous $NH_4Cl$ solution, twice with 100 ml of saturated aqueous $NaHCO_3$ and once with 100 ml of brine. The organic extracts were dried ($Na_2SO_4$), filtered, and the solvent removed on the rotary evaporator. The phenylethyl alcohol was then removed by distillation under high vacuum. The resulting residue was purified using preparative HPLC (silica gel, 4% methanol in ethyl acetate as the loading solvent and eluent). The appropriate fractions were combined, and the solvent removed to yield 0.72 g of 1,2,3,3a,8,8a-hexahydro-α-oxo-1,3a,8-trimethyl-5-pyrrolo[2,3-b]indole acetic acid, phenylethyl ester, as an oil.

| Analysis: | | | |
|---|---|---|---|
| Calculated for $C_{23}H_{26}N_2O_3$: | 72.99% C | 6.92% H | 7.40% N |
| Found: | 72.82% C | 6.85% H | 7.44% N |

EXAMPLE 6

1,2,3,3a,8,8a-Hexahydro-α-oxo-1,3a,8-trimethyl-5-pyrrolo[2,3-b]indole acetic acid, isopropyl ester To a chilled (0° C.), stirred solution of 1,2,3,3a,8,8a-hexahydro-α-oxo-1,3a,8-trimethyl-5-pyrrolo[2,3-b]indole acetic acid, ethyl ester (0.68 g) in anhydrous isopropyl alcohol (10.2 ml) was added titanium (IV) ethoxide (0.17 ml) via syringe under a nitrogen atmosphere. The solution was warmed to room temperature and refluxed for 6.5 hours. The isopropyl alcohol was removed under reduced pressure and the residue dissolved in ethyl acetate (100 ml). The solution was washed twice with 50 ml portions of saturated aqueous $NH_4Cl$ solution, twice with 50 ml portions of saturated aqueous $NaHCO_3$ solution and once with 50 ml of brine. The organic and aqueous phases were separated and the organic phase dried ($Na_2SO_4$), filtered, and concentrated to an oil. The crude mixture was purified using preparative HPLC (silica gel, 35% ethyl acetate in dichloromethane as the loading solvent and eluent). The appropriate fractions were combined and the solvents were removed under reduced pressure yielding 0.54 g of 1,2,3,3a,8,8a-hexahydro-α-oxo-1,3a,8-trimethyl-5-pyrrolo[2,3-b]indole acetic acid, isopropyl ester, as an oil.

Analysis:

| | | | |
|---|---|---|---|
| Calculated for $C_{18}H_{24}N_2O_3$: | 68.33% C | 7.65% H | 8.85% N |
| Found: | 68.31% C | 7.64% H | 8.74% N |

EXAMPLE 7

1,2,3,3a,8,8a-Hexahydro-α-oxo-1,3a,8-trimethyl-5-pyrrolo[2,3-b]indole acetic acid, diisopropyl amide To a solution of TMEDA (2.85 ml) in anhydrous ether (5.0 ml) was added at −78° C. under $N_2$ atmosphere, sec-butyllithium (14.5 ml). The resulting solution was subsequently treated with a solution of 5-bromo-1,2,3,3a,8,8a-hexahydro-1,3a,8-trimethylpyrrolo[2,3-b]indole (3.80 g) in anhydrous ether (10 ml). The mixture was held at this temperature for 3 hours and then added to a solution of diisopropylamino-oxoacetic acid, ethyl ester (7.5 g) in anhydrous ether (15 ml). After stirring at −78° C. for 4 hours, the reaction mixture was quenched with 50 ml of aqueous $NH_4Cl$ solution. The organic and aqueous phases were separated and the organic phase washed successively with saturated aqueous $NaHCO_3$ and brine. The organic phase was dried ($Na_2SO_4$), filtered and concentrated to an oil which was purified by HPLC (silica gel, 10% MeOH in ethyl acetate as eluent). 2.8 g of 1,2,3,3a,8,8a-Hexahydro-α-oxo-1,3a,8-trimethyl-5-pyrrolo[2,3-b]indole acetic acid, diisopropyl amide was obtained as a foam. Trituration with hexane and drying under reduced pressure yielded an analytically pure sample.

Analysis:

| | | | |
|---|---|---|---|
| Calculated for $C_{22}H_{33}N_3O_2$: | 70.55% C | 8.74% H | 11.75% N |
| Found: | 70.34% C | 8.95% H | 11.67% N |

EXAMPLE 8

1,2,3,3a,8,8a-Hexahydro-α-oxo-1,3a,8-trimethyl-5-pyrrolo[2,3-b]indole acetic acid To a 0° C. solution of 1,2,3,3a,8,8a-hexahydro-α-oxo-1,3a,8-trimethyl-5-pyrrolo[2,3-b]indole acetic acid, ethyl ester (0.25 g) in 95% ethanol (1.0 ml) was added a solution of 0.14 g of KOH in water (1.0 ml). The mixture was stirred at 0° C. for 30 minutes and then refluxed for 4 hours. The solution was cooled, the ethanol was removed under reduced pressure and the remaining aqueous residue was diluted with water (3.0 ml), cooled to 0° C. and neutralized with a 1.0N aqueous HCl solution. The water was then removed and the residue was taken up in dichloromethane and washed with water to remove any unreacted starting material. The aqueous washes were then concentrated to afford 1,2,3,3a,8,8a-hexahydro-α-oxo-1,3a,8-trimethyl-5-pyrrolo[2,3-b]indole acetic acid as a solid.

EXAMPLE 9

1,2,3,3a,8,8a-Hexahydro-α-oxo-1,3a,8-trimethyl-5-pyrrolo[2,3-b]indole acetic acid, 4-methoxyphenylmethyl ester To a chilled (0° C.) solution of 1,2,3,3a,8,8a-hexahydro-α-oxo-1,3a,8-trimethyl-5-pyrrolo[2,3-b]indole acetic acid, ethyl ester (2.07 g) in anhydrous 4-methoxyphenylmethyl alcohol (40 ml) was added titanium (IV) ethoxide (0.54 ml) with stirring under nitrogen atmosphere. The reaction mixture was heated without reflexing for 8 hours. The 4-methoxyphenylmethyl alcohol was removed by distillation under high vacuum and the residue was dissolved in dichloromethane (200 ml). The residue was washed successively with two 100 ml portions of saturated aqueous $NH_4Cl$ solution, two 100 ml portions of saturated aqueous $NaHCO_3$ solution and with brine, dried ($Na_2SO_4$), filtered and evaporated to yield an oil. The oil was purified by preparative HPLC (silica gel, 3% methanol in ethyl acetate as the loading solvent and eluent). A second preparative HPLC purification using 3% methanol in dichloromethane, yielded 1,2,3,3a,8,8a-hexahydro-α-oxo-1,3a,8-trimethyl-5-pyrrolo[2,3-b]indole acetic acid, 4-methoxyphenylmethyl ester (0.84 g) as an oil.

Analysis:

| | | | |
|---|---|---|---|
| Calculated for $C_{23}H_{26}N_2O_4$: | 70.03% C | 6.64% H | 7.10% N |
| Found: | 70.01% C | 6.59% H | 7.00% N |

EXAMPLE 10

1,2,3,3a,8,8a-Hexahydro-α-oxo-1,3a,8-trimethyl-5-pyrrolo[2,3-b]indole acetic acid, 4-chlorophenylethyl ester To a chilled (0° C.) solution of 1,2,3,3a,8,8a-hexahydro-α-oxo-1,3a,8-trimethyl-5-pyrrolo[2,3-b]indole acetic acid, ethyl ester (1.18 g) in 4-chlorophenylethyl alcohol (31 ml) was added titanium (IV) ethoxide (0.30 ml) under a nitrogen atmosphere with stirring. The mixture was gently heated without refluxing for 4 hours. The 4-chlorophenylethyl alcohol was removed by distillation under high vacuum and the crude residue was dissolved in dichloromethane (20 ml) and washed successively with two 100 ml portions of saturated ammonium chloride solution, two 100 ml portions of saturated sodium bicarbonate solution and 100 ml of brine.

The organic phase was dried (Na₂SO₄) filtered, and purified using preparative HPLC (silica gel, 3% methanol in dichloromethane as the loading solvent and eluent). The appropriate fractions were combined and the solvent removed under vacuum. Concentration of the appropriate fractions yielded 0.87 g of 1,2,3,3a,8,8a-hexahydro-α-oxo-1,3a,8-trimethyl-5-pyrrolo[2,3-b]indole acetic acid, 4-chlorophenylethyl ester as an oil.

Analysis:

| | | | |
|---|---|---|---|
| Calculated for $C_{23}H_{25}ClN_2O_3$: | 66.90% C | 6.10% H | 6.78% N |
| Found: | 67.00% C | 6.08% H | 6.75% N |

EXAMPLE 11

1,2,3,3a,8,8a-Hexahydro-α-oxo-1,3a,8-trimethyl-5-pyrrolo[2,3-b]indole acetic acid, n-pentyl ester A solution of 1,2,3,3a,8,8a-hexahydro-α-oxo-1,3a,8-trimethyl-5-pyrrolo[2,3-b]indole acetic acid, ethyl ester (2.89 g) in 1-pentanol (61 ml) was treated at 0° C. under a nitrogen atmosphere with titanium (IV) ethoxide (0.80 ml). The solution was warmed to room temperature and then slowly heated for 2.5 hours keeping the temperature between 60°-80° C. The excess 1-pentanol was removed by distillation under high vacuum. The residue was washed successively with 50 ml of saturated aqueous NH₄Cl solution, two 100 ml portions of saturated aqueous NaHCO₃ solution and 50 ml of brine. The organic phase was dried (Na₂SO₄), filtered and concentrated to afford an oil which was purified by chromatography using preparative HPLC (silica gel, 5% methanol in ethyl acetate). The appropriate fractions were combined and concentrated under vacuum to yield 2.2 g of 1,2,3,3a,8,8a-hexahydro-α-oxo-1,3a,8-trimethyl-5-pyrrolo[2,3-b]indole acetic acid, n-pentyl ester as an oil.

Analysis:

| | | | |
|---|---|---|---|
| Calculated for $C_{21}H_{30}N_2O_3$: | 69.74% C | 8.19% H | 8.13% N |
| Found: | 69.47% C | 8.15% H | 8.07% N |

EXAMPLE 12

1,2,3,3a,8,8a-Hexahydro-α-oxo-1,3a,8-trimethyl-5-pyrrolo[2,3-b]indole acetic acid, n-hexyl ester To a stirred solution of 1,2,3,3a,8,8a-hexahydro-α-oxo-1,3a,8-trimethyl-5-pyrrolo[2,3-b]indole acetic acid, ethyl ester (3.0 g) in n-hexyl alcohol (73.6 ml) was added at 0° C. under a nitrogen atmosphere, titanium IV ethoxide (0.83 ml). The mixture was warmed to room temperature and heated for 2 hours keeping the temperature between 60°-80° C. The excess n-hexyl alcohol was removed by distillation under high vacuum. The residue was taken up in ethyl acetate, washed twice with 100 ml portions of saturated aqueous NH₄Cl solution, twice with 100 ml portions of saturated aqueous NaHCO₃ solution and once with 100 ml of brine. The organic phase was dried (NaSO₄), filtered, and concentrated to afford an oil which was purified using preparative HPLC (silica gel, 3% methanol in dichloromethane as the loading solvent and eluent). The appropriate fractions were combined and the solvents removed under reduced pressure yielding 2.93 g of 1,2,3,3a,8,8a-hexahydro-α-oxo-1,3a,8-trimethyl-5-pyrrolo[2,3-b]indole acetic acid, n-hexyl ester, as an oil.

Analysis:

| | | | |
|---|---|---|---|
| Calculated for $C_{21}H_{30}N_2O_3$: | 70.36% C | 8.44% H | 7.81% N |
| Found: | 70.28% C | 8.44% H | 7.81% N |

EXAMPLE 13

1,2,3,3a,8,8a-Hexahydro-α-oxo-1,3a,8-trimethyl-5-pyrrolo[2,3-b]indole acetic acid, diethyl amide To a stirred (−78° C.) solution of sec-butyllithium (1.3M in cyclohexane; 6.6 ml) and TMEDA (1.3 ml) in anhydrous ether (4.0 ml) was added via canula under a N₂ atmosphere a solution of 5-bromo-1,2,3,3a,8,8a-hexahydro-1,3a,8-trimethylpyrrolo[2,3-b]indole (1.69 g), in anhydrous ether (4.0 ml). The solution was stirred at −78° C. for 2.5 hours and then added via canula, under N₂, to a stirred (−78° C.) solution of N,N-diethylamino-oxo-acetic acid, ethyl ester (3.6 g) in diethyl ether (8.0 ml). The solution was stirred at −78° C. for 3 hours and gradually allowed to warm to room temperature over 2 hours. The mixture was quenched by the addition of an aqueous solution of saturated NH₄Cl. The organic phase was separated and washed with two 50 ml portions of an aqueous solution of saturated NaHCO₃, with brine, and dried (Na₂SO₄). The crude residue was purified using preparative HPLC (silica gel, loading and eluting with 3% methanol in dichloromethane). The appropriate fractions were combined and concentrated to a foam which solidified upon trituration with hexane, to afford 1,2,3,3a,8,8a-hexahydro-α-oxo-1,3a,8-trimethyl-5-pyrrolo[2,3-b]indole acetic acid, diethyl amide.

Analysis:

| | | | |
|---|---|---|---|
| Calculated for $C_{19}H_{27}N_3O_2$: | 69.27% C | 8.26% H | 12.75% N |
| Found: | 69.05% C | 8.37% H | 12.60% N |

EXAMPLE 14

1,2,3,3a,8,8a-Hexahydro-α-oxo-1,3a,8-trimethyl-5-pyrrolo[2,3-b]indole acetic acid, n-octyl ester, citrate salt A solution of 1,2,3,3a,8a-hexahydro-α-oxo-1,3a,8-trimethyl-5-pyrrolo[2,3-b]indole acetic acid, ethyl ester (1.57 g) in anhydrous n-octanol (41 ml) was treated at 0° C. under nitrogen atmosphere with titanium (IV) ethoxide (0.58 ml). The solution was refluxed for 2.5 hours. Excess n-octanol was removed by distillation under vacuum, the residue was dissolved in ethyl acetate and washed successively with 50 ml of saturated aqueous ammonium chloride solution, two 50 ml portions of saturated aqueous sodium bicarbonate solution and 50 ml of brine. The organic phase was dried (Na₂SO₄), filtered and concentrated, the compound was purified by preparative HPLC (silica gel, using 3% methanol in ethyl acetate as the loading solvent and eluent). The appropriate fractions were combined and concentrated to an oil. The oil (0.65 mg) was dissolved in anhydrous ether (10 ml) and treated under nitrogen with one equivalent of a 0.1M ethereal citric acid solution. The solid was filtered, triturated with hexane and dried in a vacuum oven for 12 hours to yield 0.45 g of 1,2,3,3a,8,,8a-hexahydro-α-oxo-1,3a,8-trimethyl-5-pyrrolo[2,3-b]indole acetic acid, n-octyl ester, citrate salt, m.p. 96°-103° C.

| Analysis: | | | |
|---|---|---|---|
| Calculated for $C_{29}H_{42}N_2O_{10}$: | 60.19% C | 7.32% H | 4.84% N |
| Found: | 60.14% C | 7.33% H | 4.83% N |

EXAMPLE 15

1,2,3,3a,8,8a-Hexahydro-α-oxo-1,3a,8-trimethyl-5-pyrrolo[2,3-b]indole acetic acid, n-heptyl ester citrate salt To a stirred 0° C. solution of 1,2,3,3a,8,8a-hexahydro-α-oxo-1,3a,8-trimethyl-5-pyrrolo[2,3-b]indole acetic acid, ethyl ester (2.64 g) in n-heptanol (73 ml) was added under nitrogen atmosphere, titanium (IV) ethoxide (1.0 ml). The solution was heated (60°–100° C.) under $N_2$ for 2 hours. The reaction appeared complete by TLC and the excess n-heptanol was removed by distillation under high vacuum. The residue was dissolved in ethyl acetate, washed once with 50 ml of saturated aqueous $NH_4Cl$, twice with 50 ml portions of saturated aqueous sodium bicarbonate solution and once with 50 ml of brine. The organic phase was dried ($Na_2SO_4$), filtered and concentrated to an oil which was purified by preparative HPLC (using silica gel, 3% methanol in ethyl acetate as the loading solvent and eluent). An oil (2.98 g) was obtained. Formation of an analytically pure citrate salt was accomplished by treating 0.65 g of the oil in anhydrous ether (10 ml) with a 0.1M ether solution of citric acid (1.0 equiv.). The solid was filtered under a nitrogen atmosphere and dried in a vacuum oven in the presence of NaOH pellets. The solid was then triturated with hexane, filtered and dried under high vacuum for 12 hours yielding 0.63 g of 1,2,3,3a,8,8a-hexahydro-α-oxo-1,3a,8-trimethyl-5-pyrrolo[2,3-b]indole acetic acid, n-heptyl ester citrate salt, m.p. 93°–100° C.

| Analysis: | | | |
|---|---|---|---|
| Calculated for $C_{28}H_{40}N_2O_{10}$: | 59.56% C | 7.14% H | 4.96% N |
| Found: | 59.52% C | 7.17% H | 4.97% N |

EXAMPLE 16

1,2,3,3a,8,8a-Hexahydro-α-oxo-1,3a,8-trimethyl-5-pyrrolo[2,3-b]indole acetic acid, N-ethyl-N-phenylmethyl amide citrate salt monohydrate To a stirred (−78° C.) solution of anhydrous diethylether (5.0 ml), TMEDA (1.8 ml) and sec-butyllithium (11.8 ml) was added, under a nitrogen atmosphere, a solution of 5-bromo-1,2,3,3a,8,8a-hexahydro-α-oxo-1,3a,8-trimethyl-5-pyrrolo[2,3-b]indole (2.30 g) in anhydrous ether (5.0 ml). The solution was stirred at −78° C. for 2.5 hours and added via canula to a solution of N-ethyl-N-phenylmethylamino-oxo-acetic acid, ethyl ester (5.8 g) in anhydrous ether (10 ml) at −78° C. under nitrogen. The resulting mixture was stirred at this temperature for 4.5 hours and then gradually allowed to warm to room temperature. The reaction mixture was quenched with the addition of a saturated aqueous solution of ammonium chloride (100 ml). The organic phase was separated, washed with saturated aqueous sodium bicarbonate solution (2×50 ml) and brine (50 ml), dried ($Na_2SO_4$), filtered and concentrated to an oil. The material was purified by preparative HPLC (silica gel, 5% methanol in dichloromethane as the loading solvent and eluent).

The citrate salt of this material was prepared by dissolving the oil (1.15 g) in ether (10 ml) and adding 1.0 equivalent of citric acid in the form of a 0.1M solution of ethereal citric acid. A solid formed, which was filtered and dried for 2 hours in a vacuum oven in the presence of sodium hydroxide pellets. The solid was triturated with diethyl ether and dried in a drying pistol under vacuum for 12 hours which afforded 1.1 g of 1,2,3,3a,8,8a-hexahydro-α-oxo-1,3a,8-trimethyl-5-pyrrolo[2,3-b]indole acetic acid, N-ethyl-N-phenylmethyl amide citrate salt monohydrate, as a solid, m.p. 94°–120° C.

| Analysis: | | | |
|---|---|---|---|
| Calculated for $C_{30}H_{39}N_3O_{10}$: | 59.89% C | 6.53% H | 6.98% N |
| Found: | 59.99% C | 6.47% H | 6.61% N |

We claim:

1. A method of synthesizing a compound of the formula

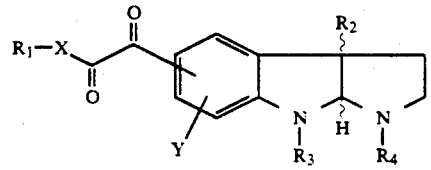

where X is —O—; $R_1$ is loweralkyl, aryl or arylloweralkyl; $R_2$ is hydrogen or loweralkyl; $R_3$ is loweralkyl or arylloweralkyl; $R_4$ is hydrogen, loweralkyl, loweralkenyl, loweralkynyl, arylloweralkyl, formyl, loweralkylcarbonyl, arylloweralkylcarbonyl or loweralkoxycarbonyl; Y is hydrogen, loweralkyl or loweralkoxy or the pharmaceutically acceptable acid addition salts thereof, and where applicable, the geometric and optical isomers and racemic mixtures thereof which comprises reacting a compound of the formula

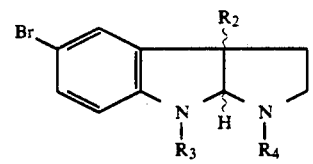

with an oxalate of the formula

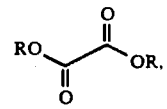

where R is loweralkyl, aryl or arylloweralkyl in the presence of N,N,N′,N′-tetramethylethylenediamine and sec-butyllithium.

2. The method of claim 1 where the dialkyl oxalate is dibutyl oxalate.

3. The method of claim 1 where the dialkyl oxalate is diethyl oxalate.

4. A method of synthesizing a compound of the formula

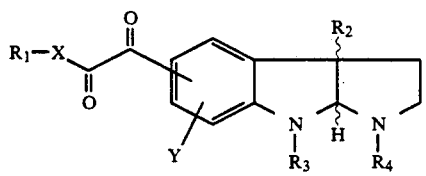

where X is —O—; $R_1$ is loweralkyl, cycloalkyl, aryl, arylloweralkyl, loweralkylene, loweralkynyl, heteroaryl selected from the group consisting of thienyl, furanyl, pyrrolyl and pyridinyl or heteroarylloweralkyl; $R_2$ is hydrogen or loweralkyl; $R_3$ is loweralkyl or arylloweralkyl; $R_4$ is hydrogen, loweralkyl, loweralkenyl, loweralkynyl, arylloweralkyl, formyl, loweralkylcarbonyl, arylloweralkylcarbonyl or loweralkoxycarbonyl; Y is hydrogen, loweralkyl or loweralkoxy or the pharmaceutically acceptable acid addition salts thereof, and where applicable, the geometric and optical isomers and racemic mixtures thereof which comprises reacting compound of the formula

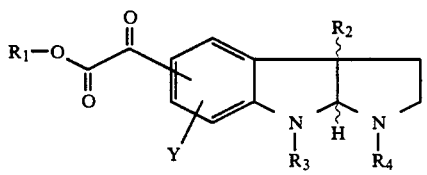

where $R_1$ is loweralkyl, with titanium ethoxide and an alcohol of the formula $R_5$—OH, where $R_5$ is loweralkyl, aryl, cycloalkyl, arylloweralkyl, loweralkylene, loweralkynyl, heteroaryl selected from the group consisting of thienyl, furanyl, pyrrolyl, pyridinyl or heteroarylloweralkyl.

5. A method of synthesizing a compound of the formula

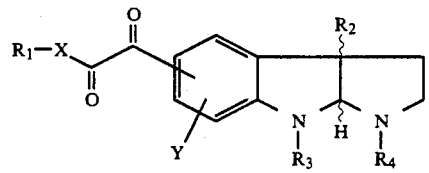

wherein X is —NH, N-loweralkyl, or N-arylloweralkyl; $R_1$ is hydrogen, loweralkyl, cycloalkyl, aryl or arylloweralkyl; $R_2$ is hydrogen or loweralkyl; $R_3$ is loweralkyl or arylloweralkyl; $R_4$ is hydrogen, loweralkyl, loweralkenyl, loweralkynyl, arylloweralkyl, formyl, loweralkylcarbonyl, arylloweralkylcarbonyl or loweralkoxycarbonyl; Y is hydrogen, loweralkyl or loweralkoxy or the pharmaceutically acceptable acid addition salts thereof, and where applicable, the geometric and optical isomers and racemic mixtures thereof which comprises reacting a compound of the formula

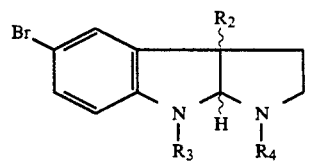

with a mixed oxalate ester amide of the formula

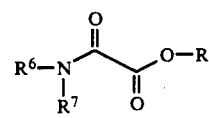

where R, $R^6$ and $R^7$ are loweralkyl, aryl or arylloweralkyl in the presence of an alkyllithium and N,N,N′,N′-tetramethylethylene diamine in an ethereal solvent.

* * * * *